United States Patent [19]
Cook et al.

[11] Patent Number: 5,797,391
[45] Date of Patent: Aug. 25, 1998

[54] INHALER

[75] Inventors: Robert Stanley Cook; Michael Anthony Hobbs; Ann-Marie Leighton; Gordon Thomas Simpkin; Roy Trunley, all of Dagenham, United Kingdom

[73] Assignee: Rhone-Poulenc Rorer Limited, West Malling, United Kingdom

[21] Appl. No.: 128,447

[22] Filed: Sep. 28, 1993

Related U.S. Application Data

[63] Continuation-in-part of PCT/GB92/00479, Mar. 18, 1992 and a continuation-in-part of PCT/GB92/00480, Mar. 18, 1992.

[30] Foreign Application Priority Data

Mar. 28, 1991 [GB] United Kingdom ............ 9106648
Mar. 28, 1991 [GB] United Kingdom ............ 9106649

[51] Int. Cl.⁶ .................. A61M 11/00; A61M 15/00
[52] U.S. Cl. .................... 128/203.15; 128/200.21
[58] Field of Search .............. 424/451; 128/203.15, 128/203.21

[56] References Cited

U.S. PATENT DOCUMENTS

| | | | |
|---|---|---|---|
| 4,069,819 | 1/1978 | Valentini et al. | 128/206 |
| 4,249,526 | 2/1981 | Dean et al. | 128/203.15 |
| 4,492,316 | 1/1985 | Emms | 221/202 |
| 5,048,514 | 9/1991 | Romella | 128/203.21 |

FOREIGN PATENT DOCUMENTS

| | | |
|---|---|---|
| 0005585 | 11/1979 | European Pat. Off. |
| 0129985 | 1/1985 | European Pat. Off. |
| 0237507 | 9/1987 | European Pat. Off. |
| 0303844 | 2/1989 | European Pat. Off. |
| 0333334 | 9/1989 | European Pat. Off. |
| 0406893 | 1/1991 | European Pat. Off. |
| 2216806 | 8/1974 | France |
| 038901 | 9/1981 | Taiwan |
| 097858 | 4/1988 | Taiwan |
| 142308 | 9/1990 | Taiwan |
| 1387954 | 3/1975 | United Kingdom |
| 1396258 | 6/1975 | United Kingdom |
| 1472650 | 5/1977 | United Kingdom |
| 1485163 | 9/1977 | United Kingdom |
| 1562732 | 3/1980 | United Kingdom |
| 2061735 | 5/1981 | United Kingdom |
| 2151491 | 7/1985 | United Kingdom |
| 07464 | 2/1989 | WIPO |

*Primary Examiner*—Raj Bawa
*Attorney, Agent, or Firm*—Ross J. Oehler

[57] ABSTRACT

An inhaler for powdered medicament in capsules has a swirling chamber which can be opened to allow access of a closed capsule into the swirling chamber for operation of capsule-opening means in the swirling chamber. Access to the swirling chamber is gained by a pivoting cover member (22) which is provided with interlock means associated with the capsule-opening means to ensure that the capsule opening means cannot be operated while the cover member is in its open position to allow access of the user's finger to the region (28) of the swirling chamber (26,28) where the capsule-opening pins (30) could damage the user's finger. A further embodiment of an inhaler has a removable capsule reservoir having a container portion (74) with a closure (76) removable to reveal the interior of said reservoir and closable to define one entire side face of said reservoir, the closure member (76) being hinged to the container portion at thin film hinge (78). The capsule container is closed by a sliding cover (16) held to the container (74) for sliding movement along a second face of the closure reservoir opposite said first face defined by the closure (76).

16 Claims, 3 Drawing Sheets

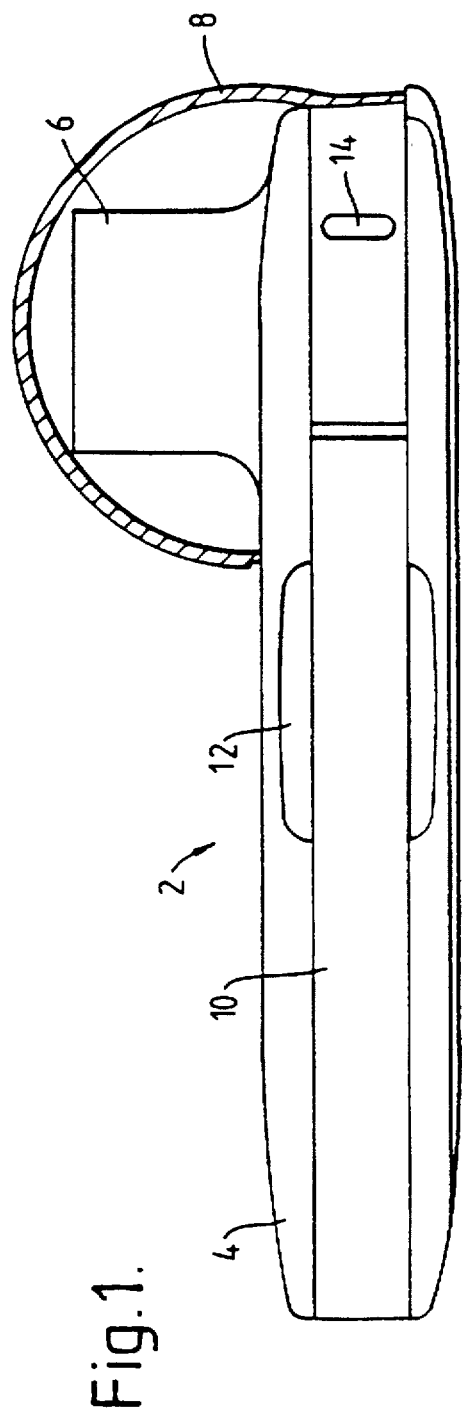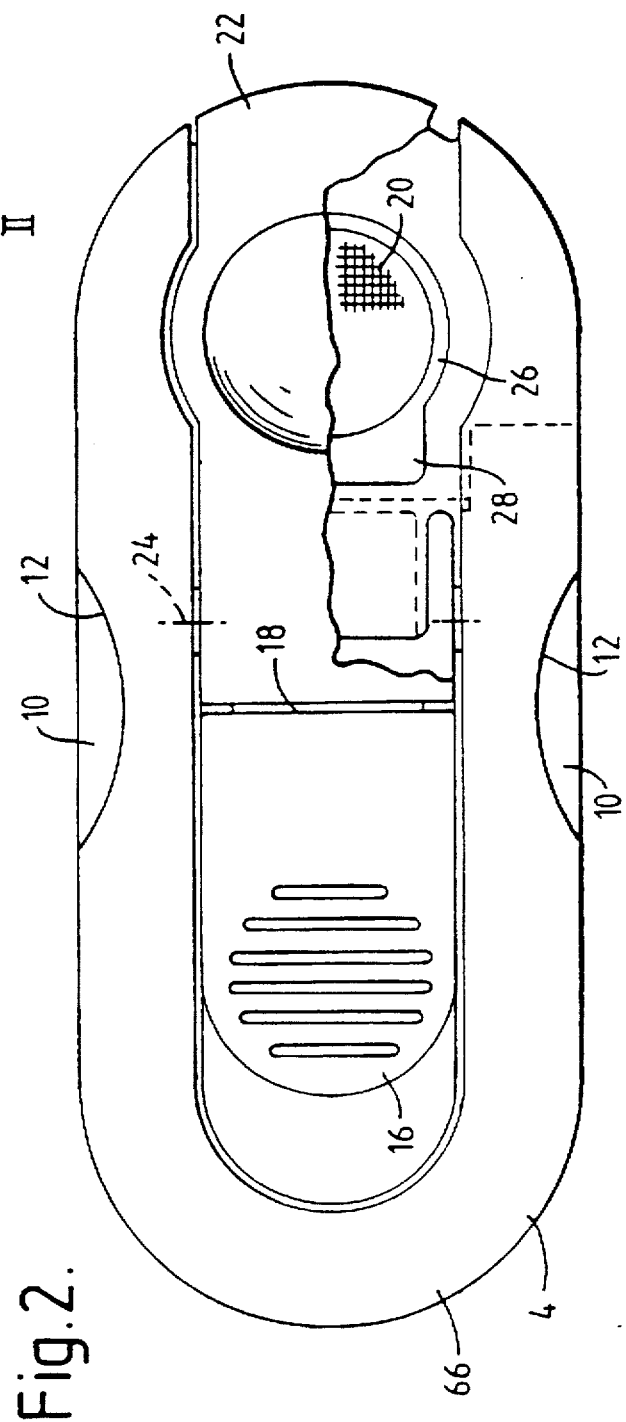

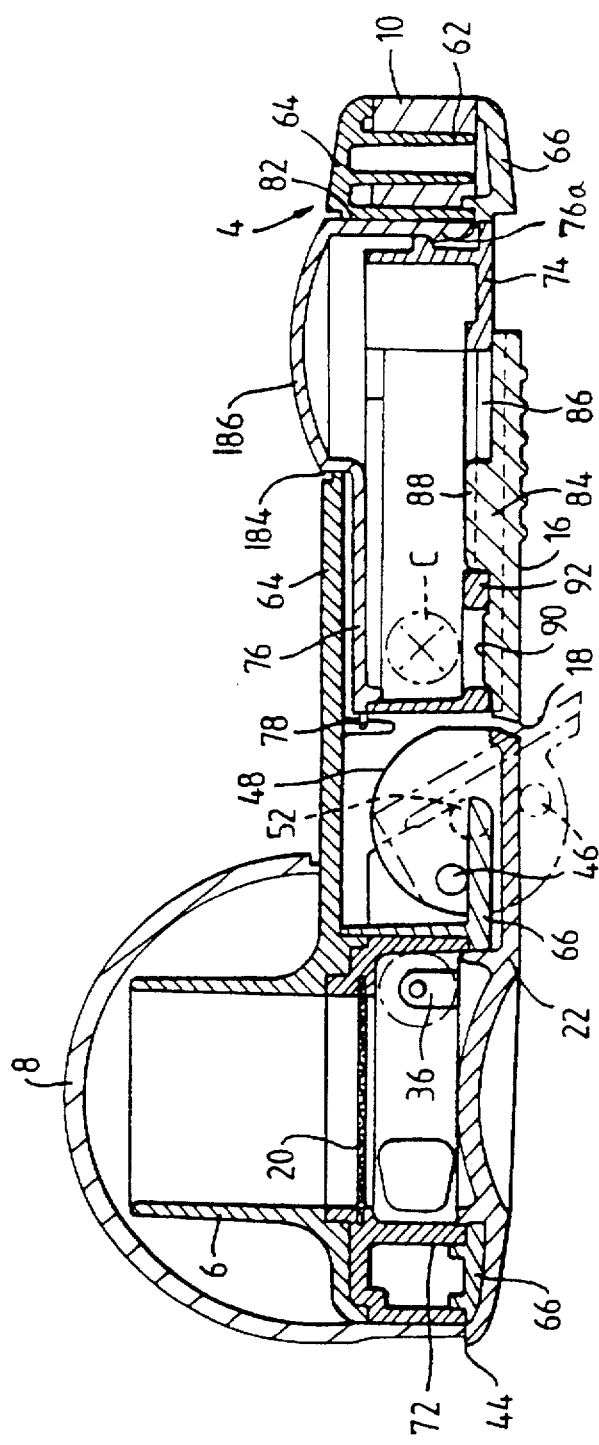

INHALER

CROSS-REFERENCE TO RELATED APPLICATIONS

This is a continuation-in-part application of our copending application Nos. PCT/GB92/00479 and PCT/GB92/00480, each filed Mar. 18, 1992.

FIELD OF THE INVENTION

The present invention relates to inhalers for allowing a patient to inhale powdered medicament, particularly from a capsule.

BACKGROUND OF THE INVENTION

Various forms of inhaler devices are known, and it is known to provide means for piercing the ends of a capsule or for separating the cap portion from the body portion of the capsule to allow medicament to be withdrawn therefrom during inhalation. Extraction of the medicament may occur as a result of the inhaled airstream passing over the capsule causing it to spin by virtue of a vortical configuration of the airstream through the inhaler. This spinning of the capsule assists ejection of the powdered medicament within the tumbling capsule to enter the inhaled airstream.

The means for piercing the medicament capsule are known to comprise pins which can be driven inwardly through the ends of the capsule, thereby puncturing the capsule by virtue of sharpened ends on the piercing pins. It is a disadvantage of the known forms of capsule-piercing inhalers that misuse of the inhaler, for example by a child, or accidental misuse by any patient may result in piercing of a human finger by operation of the capsule piercing pins. It is also a disadvantage of the known inhalers that the powdered medicament, having been ejected from the capsule, tends to agglomerate on the walls of the air passageway through the inhaler. Accordingly, even if the same inhaler is being reused by a single patient, there is a need for cleaning of the inhaler at regular intervals.

Because it is customary to open the chamber of an inhaler device to allow insertion of a fresh capsule, and because the capsule-piercing pins are typically exposed inside the chamber, such access to the chamber is sufficient to allow a finger to enter the space normally occupied by a capsule being pierced, hence leading to injury.

It is also known for an inhaler to include a reservoir for a supply of medicament capsules to be used by the patient during a given period of time, for example, one day. The existence of this reservoir of capsules complicates the task of washing the inhaler.

SUMMARY OF THE INVENTION

It is therefore an object of the present invention to facilitate washing of the parts on which powdered medicament from previous uses has agglomerated, without moistening the walls of capsules being stored for future use. It is another object of the present invention to guard against either inadvertent or deliberate misuse of the inhaler resulting in damage to a finger in the chamber. It is further an object of the present invention to overcome the above difficulty by facilitating cleaning of the reservoir.

According to a first embodiment of the present invention, an inhaler 2 for inhaling powdered medicament from capsules which are opened in the inhaler, comprises a swirling chamber for holding a capsule from which the powdered medicament is extracted by rotation of the opened capsule in the inhalation airflow through the swirling chamber; means 30 in the swirling chamber for opening a capsule having been inserted in the swirling chamber ready for inhalation; a closure member 22 movable between a first position closing the swirling chamber and a second position 22 providing access to the swirling chamber for insertion of a capsule, and interlock means (38,46,48) responsive to positioning of the closure member in said second position for inhibiting operation of said closure opening means.

According to another embodiment of the present invention, an inhaler for powdered medicament contained in closed capsules, comprises a body portion defining a swirling chamber in which an opened capsule can be rotated by vortical inhalation airflow, and a removable capsule reservoir (74,76) to hold a supply of capsules in a dry condition ready for future use, wherein the capsule reservoir adapted to be received within a housing (64) of the inhaler and is removable from the housing to allow the inhaler to be washed. The reservoir includes a slideable cover (16) to allow removal of the capsules one at a time.

BRIEF DESCRIPTION OF THE DRAWINGS

The foregoing summary, as well as the following detailed description of preferred embodiments, will be better understood when read in conjunction with the appended drawings. For the purpose of illustrating the invention, there is shown in the drawings embodiments, which are presently preferred. It is to be understood, however, that the invention is not limited to the precise arrangements and instrumentalities shown. In the drawings:

FIG. 1 is a side elevational view of an inhaler in accordance with the present invention, showing a cover over the mouthpiece sectioned to facilitate appreciation of the mouthpiece itself;

FIG. 2 is an elevational view taken along the direction of arrow 11 in FIG. 1;

FIG. 5 is a sectional view taken on the line V—V of FIG. 3; and

FIG. 6 shows a detail of a modified form of the inhaler, which is to be assembled by catch engagement.

DETAILED DESCRIPTION OF PREFERRED EMBODIMENTS

Figure 3:
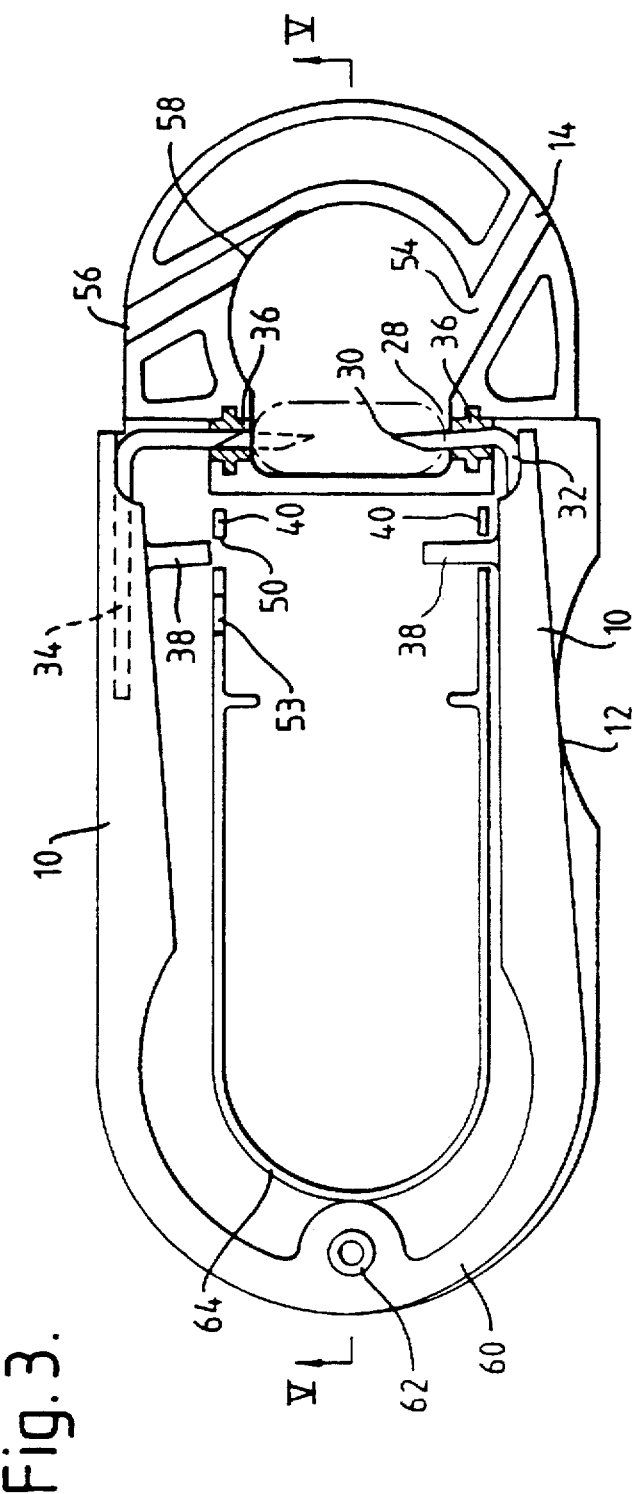
FIG. 3 is a sectional view showing on the right-hand side the position of a capsule-piercing pin during the capsule rupturing operation, and on the left-hand side the capsule-piercing pin retracted.

In the drawings, wherein like numerals are used to indicate like elements throughout, there is shown in FIG. 1 an inhaler 2 comprising a main body 4 having a mouthpiece 6 closed by a cover 8 which is a friction-fit on the inhaler body. Along each side of the inhaler body 4 there can be seen a limb of a U-shaped spring 10 which can be squeezed towards the other limb by applying pressure between the finger and thumb of the user resting in register with arcuate recesses 12 also shown in FIGS. 2 and 3.

FIG. 1 also shows, at the top of the main body 4, an air inlet 14 which forms one of two air inlets to a swirling chamber where the ruptured capsule is subjected to a vortical motion to spin the capsule and to impact it against the walls of the chamber to eject the powdered medicament from the interior of the capsule. In order to enhance the swirling action of the capsule, the chamber has opposed top and bottom walls (see FIGS. 5 and 6) giving it a generally flat cylindrical form with the axial dimension slightly greater than the diameter of a capsule but considerably less than the length of a capsule and with a diameter of the chamber in excess of the length of a capsule. The type of capsule which is conventionally used for storing powdered medicament is formed of a capsule body and a capsule cap, both normally of gelatin material, which fit together with the capsule cap over the capsule body, giving the finished capsule the shape of a generally cylindrical body having hemispherical domed ends. By "diameter" of the capsule we mean the diameter of the generally cylindrical central portion of the assembled capsule, and by "length" of the capsule, we mean the total length of the generally cylindrical central portion and its two domed ends.

Although the preferred embodiment of the present invention described herein opens the capsule by rupturing its ends, the invention is equally applicable to an alternative construction of capsule inhaler in which means are provided for drawing apart the capsule cap and the capsule body in order to open the capsule to liberate the powdered medicament contents.

The front elevational view shown in FIG. 2, viewed along the direction of the arrow 11 of FIG. 1, shows the exposed parts of the limbs of the U-shaped spring 10 visible at the arcuate recesses 12 in the main body portion 4.

Figure 4:
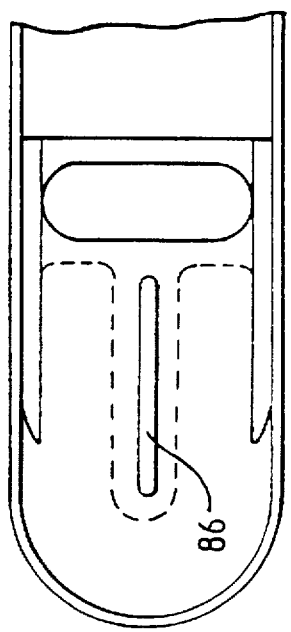
FIG. 4 is an elevational view of a removable capsule reservoir used in the device of FIGS. 1 to 3.

FIG. 2 also shows a sliding cover 16 of a removable capsule reservoir box to be described in more detail with reference to FIGS. 4 and 5. Sliding the cover 16 downwardly from the position shown in FIG. 2 retracts the top edge 18 of the lid to expose one end of the capsule reservoir box interior for release of a capsule from the normally closed reservoir.

FIG. 2 also shows, in a partly cut-away region of the inhaler, a screen grid 20 on the wall of the chamber nearer the mouthpiece 6, in order to avoid fragments of the capsule from entering the mouthpiece and hence the respiratory tract of the patient. The screen 20 is also shown in FIG. 5.

FIG. 2 also shows a cover 22 which can be opened by pivoting about a hinge line 24 for exposing the interior of the swirling chamber. The chamber comprises a generally cylindrical portion 26 having a tangentially arranged recess 28 for receiving a capsule to be pierced in the chamber. The piercing mechanism will be described later, with reference to FIG. 3, but it is important to note that the present invention provides for a preferred positioning of the capsule-opening means as a pair of piercing pins operating inside the chamber 26,28 so that there is no need for the capsule to be inserted into the swirling chamber while its ends are open.

As explained above, in the relaxed configuration, the limbs of the spring 10 are evident in the arcuate recesses 12, and FIG. 2 shows that both limbs of the spring are substantially flush with the right-hand edges of the main body 4.

FIG. 3 shows the left-hand limb of the spring 10 in this position but the right-hand limb 10 has been pressed inwardly so as to cause the sharp tip 30 of the capsule-piercing pin 32 carried by the depressed limb of the spring 10 to move inwardly of the recess portion 28 of the chamber to pierce the capsule there shown in chain-dotted lines. Also shown in chain-dotted lines, on the left-hand side of FIG. 3, is the sharp tip of the opposite capsule-piercing pin in its capsule position.

As shown in dotted lines on the left-hand side of FIG. 3, the capsule-piercing pin 32 is generally L-shaped and has a portion 34, shown in broken lines embedded in the limb of the spring while the substantially right-angle bend and the other limb of the spring project towards the recess portion 28 of the chamber. In order to guide the pins during their capsule-piercing movement, particularly bearing in mind the fact that the hemispherical domed end of the capsule will tend to deflect the sharpened tip 30 of the pins sideways as the two pins begin to press against the domed ends of the capsule, the two capsule-piercing pins are guided in respective locator bodies 36 which are positioned as close as possible to the position of the capsule in the recess 28 in order to ensure positive centring of the pins 32 during capsule piercing.

The right-hand side of FIG. 3 shows that a stud 38 integrally formed with the limb of the spring 10 has moved inwardly of the body of the inhaler through a hole 50. By contrast, the stud 38 of the left-hand limb of the spring is clear of the space between two walls 40 of the inhaler body 4 and is retracted with its tip in the hole 50.

The purpose of the two studs 38 is to provide an optional interlock between the limbs of the spring 10 and the cover 22 which can be opened to allow access to the swirling chamber for permitting loading of a capsule in the swirling chamber recess ready for piercing.

As shown in FIG. 5, the upper end 44 of the cover 22 protrudes from the adjacent surface of the inhaler body to allow the user to place a thumb or a fingernail behind the upper end 44 to pull the cover 22 into an open or "second" position 22' configuration partly shown in chain-dotted lines in FIG. 5.

As also shown in chain-dotted lines and in solid lines in its closed or "first" position, the cover 22 there is an optional hole 46 of a generally semi-circular ear 48 of the cover 22. Each side of the cover has a separate such ear 48, each provided with its respective hole 46, and the two holes 46 register with similar holes 50 in the wall portions 40 but only when the cover 22 is in its closed position shown in full lines in FIG. 5. In all other positions of the cover 22, which is pivotable about the axis 24 (FIG. 2) by virtue of pivot lugs 52 shown in chain-dotted lines in FIG. 5, the ears 48 are immediately adjacent, and between, the walls 40 and close off the holes 50, thereby preventing the limbs of the U-shaped spring 10 from being squeezed together into the position shown on the right of FIG. 3. Hence, because the studs 38 are unable to move towards one another, equally the sharpened tips 30 of the capsule-piercing pins 32 are located in the position shown on the left-hand side of FIG. 3, i.e. fully retracted into the locators 36 where there can be no risk of inadvertent piercing of the finger of a user.

It is alternatively possible for the optional holes 46 to be omitted and for the ears 48 to be of different shape which will allow the operation of the capsule-piercing pins during positions other than the fully closed position of the cover 22, but the preferred arrangement shown in FIG. 5 is considered the safest one where the optional holes 50 are provided and will be closed off at all times other than when the cover 22 is fully home.

The risk of such piercing of the user's finger can arise not only through deliberate misuse of the device by a child playing with it, or through accidental misuse of the device by either an adult or a child, but also through normal manipulation of the device to clean the swirling chamber 26,28 of agglomerated powdered medicament resulting from previous uses of the inhaler. In view of the need to clean the device, it is an advantage to have the interlock to prevent the capsule-piercing pins from entering the recess 28 while there is access to the chamber.

The shape of the swirling chamber, with its generally cylindrical portion 26 and its generally tangential capsule-receiving recess 28 where the capsule-opening means are effective, is disclosed in our co-pending British Patent Application No. 90 13261.4 and is considered highly advantageous in resulting in both (i) centrifugal ejection of the contents through the swirling action of the vortical inhalation airflow entraining the capsule to cause it to tumble or spin within the chamber, and also (ii) percussive ejection as the ends of the capsule knock against the non-circular chamber side wall, particularly at the obtuse corners between the recess 28 and the generally cylindrical chamber portion 26. It is also disclosed in our said British Application No. 90 13261.4 that the generally flat nature of the chamber results in the capsule always being held in the same plane (the median plane of the chamber) in order to enhance the regularity and the intensity of the rotational tumbling of the capsule to eject the powdered medicament centrifugally.

FIG. 3 shows the two air passages into the swirling chamber, one of them tangentially inwardly from the air inlet 14 also shown in FIG. 1, and opening generally tangentially into the generally cylindrical chamber 26 at a port 54 from which the entering air stream will strike the capsule (shown in chain-dotted lines in FIG. 3 to assist in ejecting the capsule from the capsule-rupturing recess 28 (bearing in mind that by now the two pin tips 30 will have been retracted into the locators 36) thereby liberating the capsule for entrainment in the vortical flow within the chamber 26.

The other air inlet 56 communicates with a passage to a port 58 discharging the inhaled air tangentially along a direction which is non-parallel with respect to the direction of air from the port 54 mentioned above.

As shown in FIG. 3, the bight 60 of the U-shaped spring 10 is secured to the main body It of the inhaler by means of a hollow stud 62 also shown in FIG. 5. In practice, the main body portion It consists of a front part 64 in which the mouthpiece 6 is formed, and a rear piece 66 which may be bonded to the front piece 64, for example, by ultrasonic welding of the two parts 64.66 of the body portion 4 at their inter-engaging regions. As an alternative, it is possible for the two parts 64,66 of the main inhaler body It to be secured together by a catch engagement means providing a snap fit which will facilitate assembly of the inhaler body. A detail of such a variation is shown in FIG. 6 where the components which are also shown in FIG. 5 are given the same reference numerals and the catch detent features 68 are also shown.

It will, of course, be understood that the grid screen 20 is embedded in the chamber-defining portion 72 preferably from the time of its manufacture. Alternative methods exist. For example the grid may be insert-molded into a containing ring which is then inserted into the mouthpiece.

To minimize the extent to which the released powdered medicament can agglomerate on the surface of the air passage through the inhaler, the chamber portion 72 is preferably formed of a polymer having low surface resistivity, thereby having anti-static properties. Preferably, the material defining the inside wall of the chamber 26,28 is a polymer having a surface resistivity of less than about $10^{12}$ Ohms or more preferably less than about $10^8$ Ohms. In the present embodiment, the entire chamber defining body portion 72 is formed of the same low surface resistivity polymer, but if desired the chamber is provided with an inner lining of the low surface resistivity material.

The term "anti-static material" as defined herein is intended to denote a material which does not readily exert an electrostatic attraction for the powdered medicament released into the inhaler from the opened capsule. The anti-static properties may be derived by having a wall surface of a high static dissipativity on, and/or by having a high electrical conductivity, and/or by having a low surface resistivity.

There are various additives known to increase the anti-static properties of polymers, for example by increasing the electrical conductivity or reducing the surface resistivity, or enhancing the static dissipativity properties. One possibility is to incorporate carbon or steel filler, often in the form of fibers, into the polymer used for manufacture of those components to be given enhanced anti-static properties. This enhances the electrical conductivity and/or lowers the surface resistivity. Alternatively non-fibrous chemical additives, often blended into the molding polymer in chip form prior to the molding process, may be used to lower the surface resistivity in the molded product. The product PEBAX manufactured by Atochem of France is a polyether block amide product which may be obtained in an anti-static grade by use of such additives.

Another possibility is for the molded component to be coated with an electrically conducting layer which thus reduces the surface resistivity to the levels discussed above. More preferably, but optionally, the mouthpiece 6 has its inner wall formed of such a material and more preferably still, the cover 22 which closes the back of the swirling chamber may be itself formed of such a low surface resistivity polymer.

FIG. 5 shows the removable capsule reservoir box as comprising a box portion 74 and a lid 76 hingeably connected thereto by means of a thin film hinge 78. The box includes the sliding cover 16 mentioned above, and is held in place in the device by being a friction fit between the bottom surface 82 of the box and the engaging face of the front body portion 64 of the inhaler and also between the upper edge surface 184 of a domed portion 186 of the lid 76 and the abutting edge of the recess in the inhaler front body portion 64 which receives that domed cover portion 186.

The purpose of removing the capsule reservoir 74,76 is to allow the reservoir to be removed and kept dry while the rest of the device is being washed to clear any build-up of agglomerated powdered medicament from the walls of the inhalation air passage. In this way, the reservoir 74,76 which does not ever become exposed to the powdered medicament (because the capsules contained in the reservoir are always closed) can be kept apart from those parts of the inhaler which need to be washed in order to remove agglomerated medicament. Then, when the washed parts of the device have been thoroughly dried, ready for future use, the reservoir box can be reinserted.

Another advantage of being able to remove the reservoir is that this allows the pharmacist to dispense a package comprising the capsules already contained in a reservoir which can then simply plug into the inhaler in place of an empty reservoir which can either be disposed of or recycled.

If the reservoir 74,76 is to be reused, then replenishment of its supply of capsules is achieved by first of all removing the reservoir 74,76 from the rest of the inhaler 2 and then opening the lid 76 to expose the interior or the reservoir box 74. If, inadvertently, any of the capsules have become moist and the gelatin body of the capsule has begun to soften and become sticky, then such capsules can be readily removed when the lid 76 has been opened. A fresh supply of capsules is then inserted in the box 74 and the lid 76 is then closed and the reservoir once more inserted into the inhaler 2.

As indicated above, the sliding cover 16 is part of the reservoir and can be drawn downwardly to liberate a top capsule, shown at C in FIG. 5. For this purpose, the sliding cover 16 has a shoe 84 dimensioned so as to be received within a slot 86 of the box 74 and having a wider edge portion 88 which is able to be forced through the slot 86 but then prevents removal of the slide 16 from the box 74 by virtue of the edge portion 88 being too wide to return to the slot 86.

The sliding cover 16 is also provided with a detent shoe 90 which is able to engage over a bar 92 of the box 74 in the uppermost position of the slide but which can only pass over the bar 92 when the sliding cover 16 is pulled strongly downwardly so as to cause the slide to bend as the shoe 90 rides up over the bar 92. There will similarly be a catch engagement action holding the sliding cover in its uppermost position when the slide is again returned to the upper position. It will be appreciated that the upper and lower ends of the detent shoe 90 are chamfered in ordered to ease passage of the shoe 90 over the bar 92 in either direction of movement.

The alternative configuration illustrated in FIG. 6 is intended simply to exemplify an alternative way of assembling the inhaler and It is not envisaged that in the life of the inhaler the catches 68 will ever need to be released. The provision of those catches is intended simply to facilitate the operation of assembling the inhaler after molding.

In FIG. 6, the grid 20 is shown insert-molded in a mounting ring 70 and the mouthpiece 6 is integral with the swirling chamber-defining component. This integral component 6 is injection molded of a suitable anti-static polymeric material.

The operation of assembling the inhaler 2 shown in the drawings is performed as follows:

The grid 20, already insert-molded in the mounting ring 70 (FIG. 6), is first snapped in place (unless the grid is embedded in the chamber-defining portion 72 as in FIG. 5, or in the mouthpiece.

The two retainers 36 for the piercing pins 32 will then be slid into place in the chamber into the positions shown in FIG. 3. The integral mouthpiece and chamber component 6 is then inserted into the front cover 64.

The pins 32,34 are inserted into the spring 10.

Then the U-shaped spring 10 and the front body portion 64 of the inhaler body are fastened together by insertion of the hollow stud 62 of the front body portion 64 into the socket provided in the bight of the spring 10. With the spring in the open position (as shown at the left-hand side of FIG. 3) the cover 22 is then snapped in place with the pivot lugs 52 of the ears 48 inserted between the two wall portions 40 snapping into place in the holes 53 formed to receive them.

Then, with the cover 22 in the closed position, the rear body portion 66 is offered up to the rest of the assembly and united to it either by ultrasonic welding at the points of contact between the two portions 66 and the rest of the assembly or by catch-engagement as the portion 66 is pressed against the rest of the assembly so that the catches 68 ride over the corresponding ribs such as 94 in FIG. 6 by virtue of deformation of the legs 96 on which the catches 68 are defined.

Finally, the mouthpiece cover 8 is snapped in place and the capsule reservoir 74,76 is itself forced into place. It will, of course, be understood that assembly of the sliding cover 16 to the box 74 is achieved simply by pressing the sliding cover firmly against (i.e. rightwardly as viewed in FIG. 5) the box 74 to drive the detent edge 88 of the blade 84 through the slot 86.

Although, in the above description, the mesh screen 20 is described as a stainless steel mesh, which has the advantage of being electrically conductive, the mesh can be of any other suitable optionally anti-static material which may be electrically conductive, or electrostatically dissipative or of low surface resistivity, and which is non-corrosive and will resist washing. For example, it is possible to mold a mesh integrally with the rest of the chamber-defining portion 72 as an integral component.

All the components of the inhaler may be formed by injection molding, and as will be seen the only complications are the need for embedding of the L-shaped pins 32,34 in the ends of the limbs of the spring 10, and the embedding of a mesh 20 in the chamber-defining portion 72.

The purpose of having separate retainers 36 for the support of the capsule-piercing pins 32 is to ensure that there will be no problems of trying to mold a passage (for the pin 32), having a bore which therefore closely matches the profile of the pin 32, along a direction which converges with the direction of the air passage between air inlet 14 and port 54 at the right-hand side of FIG. 3. The retainers could also act as an additional seal to avoid the ingress of air into, or the loss of powder from, the inhalation chamber.

The use of the device shown in the drawings is as follows:

Normally the device will be stored in a container, or even a pocket or handbag, with the mouthpiece cover 8 attached and all the capsules stored in the removable reservoir 74,76. When an inhalation is to be effected, the user slides the cover 16 of the reservoir 74,76 downwardly by pressure with the thumb on the thumb-grip ribs shown in FIG. 2, to expose the slot normally occupied by the chamfered blade 90 of the sliding cover 16. This is best carried out with the device already inverted so that the capsule shown at C in FIG. 5 is in position ready to leave through the slot once the sliding cover 16 has been retracted far enough.

After ejection of one capsule, such as C, the sliding cover 16 is returned to the FIG. 5 position to close off the reservoir 74,76 and then the cover 22 is opened either by catching a fingernail or the end of the thumb or finger behind the upper edge 44 and pulling the top of the cover 22 (as viewed in FIG. 5) away from the main body 4, or possibly by downward pressure on the very bottom end of the cover 22 (although this latter movement may impose too much strain on the hinge lugs 52 and is not the most straight-forward way of opening the cover 22). The capsule C can then be placed manually in the capsule-piercing recess 28 (FIG. 3) ready to be pierced by the sharpened tips 30 of the pins 32. A capsule is shown in such a position in chain-dotted lines in both FIG. 3 and FIG. 5.

The cover 22 is then once again closed and snapped shut, and only now is it possible to operate the capsule-piercing mechanism, by virtue of the holes 46 in the ears 48 having come into register with the studs 38 on the spring 10. At this stage the mouthpiece cover 8 is removed and the mouthpiece is exposed ready for inhalation.

The user then squeezes the exposed areas of the limbs of the U-shaped spring 10 at the recesses 12 (FIG. 2) to drive the pins 32 towards one another to pierce the ends of the capsule, guided by the locators 36. The capsule-piercing operation is concluded by releasing the limbs of the spring 10 to return to the FIG. 2 position (see the left-hand side of FIG. 3).

The user now places his or her lips over the mouthpiece 6 and inhales, thereby entraining an inward airflow through each of the inlets 14,56 (FIG. 3) and into the chamber 26,28 by virtue of the ports 54,58 (FIG. 3) and this airflow will generate a vortex inside the circular region 26 of the chamber which lifts the capsule from the position (shown in FIG. 3) in the recess 28 and causes it to tumble rapidly in a spinning action in which the capsule has a transverse axis substantially coincident with the axis of symmetry of the cylindrical part 26 of the chamber. The fact that there are only two ports 54 and 58, together with the fact that they are not parallel to one another, and the existence of the capsule-piercing recess 28 tangentially with respect to the cylindrical chamber 26, will all help to create a percussive impacting of the capsule on the walls of the chamber 26,28 during its rotation, thereby ejecting the powdered medicament within the capsule through the pierced ends of the capsule both as a result of centrifugal action due to the spinning of the capsule and as a result of the percussive knocking of the capsule on the walls, and in particular on the corners of the chamber walls between the capsule-shaped recess 28 and the generally cylindrical remainder 26 of the swirling chamber.

If the ends of the capsule fracture during the piercing operation and cause brittle fragments to be released, these cannot enter the respiratory tract of the user because the inhaled air and entrained pulverulent medicament from the swirling chamber must first pass through the screen 20 before entering the mouthpiece 6. This screen 20 will thus hold back any fragments of capsule, and will certainty hold back the main portion of the capsule against swallowing by the user.

Where the capsule does disintegrate in this way, the device in accordance with the present invention is well able to deal with this problem because the capsule is retained inside the swirling chamber, behind the screen 20, during both capsule piercing and inhalation, whereas in other devices, such as that of EP-A-0 333 334 the capsule is opened by pushing it against a fixed pin in the chamber before the chamber is closed, so any fragmentation of the capsule cap or capsule body will result in loss of the medicament, giving rise to an inadequate dose. In this earlier device, the problem is compounded because of the need to pierce both ends of the capsule separately, whereas in the present device, the two ends of the capsule are pierced simultaneously.

Hopefully, all the powdered medicament will pass into the respiratory tract of the user, and indeed we have found that the device in accordance with the present invention achieves high rates of removal of the powdered medicament from the capsule, and high efficiency of removal of the medicament from the inhaler as a whole, while keeping the pressure drop across the inhaler at a minimum. This low drop in pressure across the device is particularly important, bearing in mind that the principal purpose of the device is to administer a medicament to exhibit therapeutic effects on the respiratory tract of a patient whose respiratory tract is therefore already rather weak and unable to generate a strong pressure differential.

For example, at an inhalation airflow of 60 liters per minute, the device has been measured to effect a 98% efficient emptying of the powder from the capsule shell and to present a pressure drop of 26.9 cm water gauge, whereas at 30 liters per minute inhalation airflow, the efficiency of emptying the capsule has only dropped to 93%, and the pressure differential has dropped to 6.9 cm water gauge. The pressure drop at 40 liters per minute is 12.8 cm water gauge, that at 50 liters per minute it is 18.8 cm water gauge, and that at 20 liters per minute it is 2.8 cm water gauge. The fact that dropping the inhalation flow rate from 60 liters per minute to 30 liters per minute only causes a slight deterioration in the efficiency of emptying of the capsule is particularly significant because it means that those patients already having a seriously deficient respiratory function are well able to inhale a very high proportion of the total medicament available in the capsule on one inhalation.

By way of comparison the device was tested at the same flow rates, but without a capsule present in the swirling chamber and the pressure drops across the device were as shown in Table 1.

TABLE 1

| Flow rate (l/min) | 20 | 30 | 40 | 60 |
|---|---|---|---|---|
| Pressure drop (cm H$_2$O) | 3.4 | 8.0 | 14.9 | 32.9 |

Surprisingly it has been found that the pressure drop actually decreases when a capsule is present, thus aiding the inspiration by the patient.

By virtue of the low surface electrical resistivity of the appropriately selected material for the swirling chamber internal walls of the inhaler, and possibly also the mouthpiece, only a minimum of the powdered medicament remains on those walls to cause an agglomeration to build up with that resulting from subsequent uses.

However, it is nevertheless expedient to wash the air passageways from time to time and with the device illustrated this may be effected by first removing the capsule reservoir 74,76 and thoroughly washing the device, and drying it afterwards. Once the device is fully dry, the capsule reservoir 74,76 can be reinserted and the mouthpiece cover 8 reattached, to prepare the device for future storage and subsequent inhalations. It will, of course, be understood that the operations of washing and drying the swirling chamber and the mouthpiece are effected by opening the pivotal cover 22 on the back of the inhaler in order to allow access to the interior of the swirling chamber.

Although cleaning may be by wiping clean or washing, the dry cleaning operation is preferred because the presence of residual moisture will cause even more problems than any static charge on the mouthpiece and chamber.

The device in accordance with the present invention offers the further advantage in that the measured efficiencies of discharge of the powdered medicament from within the capsule are readily reproducible given the particular inhalation airflow rate applicable.

Additionally, because of the design of the chamber, the turbulent airflow generated, and the percussive action coupled with the centrifugal component of the capsule motion, the performance of the device remains fairly consistent over a wide range of inspiration rates. Table 2 shows the performance of the device.

Assessment of performance was carried out using an existing two-stage impinger, (apparatus A, described at pages A204 to A207 (Appendix XVII C) in the British Pharmacopoeia, 1988), which gives an indication of the quantity (or amount) of drug likely to reach the bronchioles and alveoli of the person using the inhaler according to the quantity of powder reaching the second stage of the impinger.

A model drug, Salbutamol sulphate was employed in the tests.

It can be seen that both delivery of drug to the lungs and reproducibility of delivery are very good and better than comparable commercial devices.

TABLE 2

Performance of the Inhaler using a B.P. Two Stage Impinger (apparatus A).

| Airflow (l/min) | (%) |
|---|---|
| (a) Percentage of Dose reaching the second stage of the impinger. | |
| 20 | 22.1 |
| 30 | 28.5 |
| 60 | 25.9 |
| (b) Reproducibility of Dose delivery; 6 successive individual capsule actuations. Result expressed as relative standard deviation (percent). | |
| 20 | 13.8 |
| 30 | 4.3 |
| 60 | 5.4 |

Hence, it is considered that the use of the device is not subject to any degree of skill or practice on the part of the operator; provided the patient ensures that the capsule is in the correct position before operating the capsule-piercing pin by squeezing the spring 10, the capsule will always be open at both ends and will always liberate an extremely high proportion of its contents, even at low inspiration rates.

The mouthpiece 6 may be integral with the chamber-defining component 72 and this would indeed be preferable as eliminating a parting line at which the powdered medicament could agglomerate.

The present invention may be embodied in other specific forms without departing from the spirit or central attributes thereof and, accordingly, reference should be made to the appended claims, rather than to the specification, as indicating the scope of the invention.

We claim:

1. An inhaler for inhaling powdered medicament from capsules which are opened in the inhaler, comprising: a swirling chamber for holding a capsule from which the powdered medicament is extracted by rotation of the opened capsule about the transverse axis of the capsule in inhalation airflow through the swirling chamber; means in the swirling chamber for opening a capsule inserted in the swirling chamber for inhalation; a closure member movable between a first position closing the swirling chamber and a second position providing access to the swirling chamber for insertion of the capsule; and interlock means responsive to positioning of the closure member in said second position for inhibiting operation of said capsule opening means, wherein said capsule opening means comprise at least one pin driveable for piercing the capsule to provide an opening through which the powdered medicament can be released during swirling.

2. An inhaler according to claim 1, wherein there are two of said pins and they are mounted to approach one another colinearly for piercing the domed ends of an elongate capsule, and in that the swirling chamber includes a recess to support said elongate capsule during operation of said pins.

3. An inhaler according to claim 1, wherein said closure member is movable from said first position to said second position by pivoting.

4. An inhaler according to claim 1, wherein said interlock means are responsive to arrival of said closure member at said first position for liberating the capsule-opening means for operation while said closure member is in said first position, and are effective to inhibit operation of said capsule-opening means, both in said second position and in all intermediate positions.

5. An inhaler according to claim 4, wherein said closure member is movable from said first position to said second position by pivoting, and wherein said closure member comprises a pair of ears each having an aperture extending therethrough for registration with a stud of said interlock means whereby said stud is unable to move in the direction corresponding to operation of said capsule-opening means until said aperture in the ears are in register with said stud.

6. An inhaler according to claim 5, wherein said ears are flexible and each include a respective pivot lug for engagement with a pivot recess of the body of the rest of the inhaler, whereby said ears may be deflected either towards or away from one another to permit entry of said pivot lugs into said pivot recesses by deformation of the ears during assembly of the inhaler, whereupon the ears then spring back to their relaxed configurations to hold the closure member connected to the rest of the inhaler body.

7. An inhaler according to claim 1, wherein the chamber is non-circular and has two opposed walls joined by at least one further wall of non-circular shape, and is able to allow the capsule to rotate freely about its transverse axis under the influence of the inhaled airflow and impact against said at least one further wall in order to increase the likelihood of ejection of the medicament from within the capsule.

8. An inhaler for powdered medicament contained in closed capsules, comprising a body portion defining a swirling chamber in which an opened capsule can be rotated by vortical inhalation airflow, and a capsule reservoir removably connected to the inhaler so as to hold the supply of closed capsules in said inhaler in a dry condition ready for future use and to allow capsules to be removed from said capsule reservoir while it is connected to the inhaler and placed in the swirling chamber for inhalation, wherein said capsule reservoir is adapted to be received within a housing of the inhaler whereby the capsule reservoir can be removed from the housing in the inhaler for allowing the inhaler to be washed, and the reservoir includes a slideable cover to allow removal of the capsules one at a time, wherein the capsule reservoir includes a cover able to be moved along the reservoir between a first position in which the capsule reservoir is closed against ingress of dirt and moisture, and second position to reveal an opening through which a capsule can be extracted for use in the swirling position.

9. An inhaler according to claim 8, wherein in the capsule reservoir includes a removable closure to provide access to the interior of the capsule reservoir for cleaning.

10. An inhaler according to claim 9, wherein said closure is hinged to said capsule reservoir by means of a thin film hinge.

11. An inhaler according to claim 9, further comprising catch engagement means for holding said closure in its closed position.

12. An inhaler according to claim 11, wherein the configuration of said closure and said catch engagement means are such that the catch engagement means cannot be released to open said closure while said capsule reservoir is in position in said housing of the inhaler.

13. An inhaler according to claim 12, wherein said closure includes a domed portion which can be depressed by the user of the inhaler to eject said capsule reservoir from the housing in said inhaler to release the capsule reservoir and to liberate said catch engagement means for operation to open said closure member.

14. An inhaler according to claim 8, wherein said cover is biased to remain in either said first position or said second position, and is slideably connected to the capsule reservoir in a manner which prevents removal of said cover from the reservoir.

15. An inhaler according to claim 8, wherein said capsule reservoir comprises a capsule container housing a plurality of elongate capsules containing powdered medicament within an openable skin, a cover mounted for sliding movement between a first position in which said capsule container is closed and a second position to reveal an opening through which one said capsule can pass at a time, said cover being mounted on a first side of the capsule container, and a closure able to close the opposite side of said capsule container and pivotally connected thereto, the arrangement being such that said capsule reservoir can be received within the housing of an inhaler.

16. An inhaler according to claim 8, wherein the chamber is non-circular defined by first and second opposed walls and at least one further wall of substantially cylindrical form with a generally tangential capsule-receiving recess therein; and is able to allow the capsule to rotate freely about its transverse axis under the influence of the inhalation airflow and otherwise to impact against said at least one further wall in order to increase the likelihood of ejection of the medicament from within the capsule.

* * * * *